(12) United States Patent
Woo

(10) Patent No.: US 11,766,632 B2
(45) Date of Patent: Sep. 26, 2023

(54) GLASS OR ALUMINUM STRUCTURE AIR FILTER USING PHOTOCATALYST PRECOAT AND MANUFACTURING METHOD THEREFOR

(71) Applicant: Tae Young Woo, Seoul (KR)

(72) Inventor: Tae Young Woo, Seoul (KR)

( * ) Notice: Subject to any disclaimer, the term of this patent is extended or adjusted under 35 U.S.C. 154(b) by 104 days.

(21) Appl. No.: 17/432,513

(22) PCT Filed: Feb. 20, 2020

(86) PCT No.: PCT/KR2020/002443
§ 371 (c)(1),
(2) Date: Aug. 20, 2021

(87) PCT Pub. No.: WO2020/175847
PCT Pub. Date: Sep. 3, 2020

(65) Prior Publication Data
US 2022/0143539 A1 May 12, 2022

(30) Foreign Application Priority Data
Feb. 27, 2019 (KR) .................... 10-2019-0023216

(51) Int. Cl.
*B01D 39/20* (2006.01)
*B01D 53/86* (2006.01)
*B01D 53/88* (2006.01)

(52) U.S. Cl.
CPC ..... *B01D 39/2003* (2013.01); *B01D 39/2027* (2013.01); *B01D 53/8668* (2013.01); *B01D 53/885* (2013.01); *B01D 2239/0478* (2013.01); *B01D 2239/083* (2013.01); *B01D 2239/10* (2013.01); *B01D 2255/20707* (2013.01); *B01D 2255/9022* (2013.01); *B01D 2258/06* (2013.01); *B01D 2259/804* (2013.01)

(58) Field of Classification Search
CPC ............ B01D 39/2003; B01D 39/2027; B01D 53/8668; B01D 53/885; B01D 2239/0478; B01D 2239/083; B01D 2239/10; B01D 2255/20707; B01D 2255/9022; B01D 2258/06; B01D 2259/804; A61L 9/16; A61L 9/18; A61L 9/20; A61L 2209/00; A61L 2209/10
See application file for complete search history.

(56) References Cited

U.S. PATENT DOCUMENTS

| 2014/0017135 A1* | 1/2014 | Boodaghians ......... A61L 9/205 422/121 |
| 2018/0179079 A1* | 6/2018 | Lu ........................ B29C 49/071 |
| 2020/0360858 A1* | 11/2020 | Mathur ................... A61L 9/205 |

FOREIGN PATENT DOCUMENTS

| JP | 2000 225 339 A | * | 8/2000 | ............... C09D 5/00 |
| JP | 2002-316021 | | 10/2002 | |
| JP | 2004-181301 | | 7/2004 | |
| JP | 2018-171620 | | 11/2018 | |
| KR | 10-0922254 | | 10/2009 | |
| KR | 10-2009-0124425 | | 12/2009 | |
| KR | 10-2011-0013921 | | 2/2011 | |
| KR | 10-2021420 | | 9/2019 | |
| WO | 2002006159 | | 1/2002 | |
| WO | WO 2014/003446 A1 | * | 1/2014 | ............. B01D 53/86 |

\* cited by examiner

*Primary Examiner* — Timothy C Vanoy
(74) *Attorney, Agent, or Firm* — LEX IP MEISTER, PLLC

(57) ABSTRACT

The present invention relates to an air filter using glass and aluminum substrates coated with a photocatalyst and a manufacturing method therefor. Disclosed is an air filter, which is more efficient in removing organic gas from air by using optical properties of a glass material and surface reflectance of an aluminum metal material to actively utilize the transmission and reflection of the light that is limitedly provided.

8 Claims, 5 Drawing Sheets

GLASS OR ALUMINUM STRUCTURE AIR FILTER USING PHOTOCATALYST PRECOAT AND MANUFACTURING METHOD THEREFOR

TECHNICAL FIELD

The present invention relates to a photocatalytic air filter employing a glass structure or aluminum honeycomb structure to which a colloidal photocatalytic precoat is applied and a manufacturing method thereof, and more particularly, to an air filter used inside an air purifier, which includes a photocatalyst and a filter structure for accommodating the photocatalyst, and a technique for improving the persistence of a photocatalytic effect and the photoactivation efficiency of the photocatalyst by improving surface bonding between the filter structure and the photocatalyst.

That is, in the present invention, a photocatalytic air filter which has improved performance due to including a colloidal photocatalytic precoat capable of forming a strong bonding layer between a photocatalytic layer with high photoactivity that forms an outermost surface layer and a surface of a filter structure is provided.

In particular, the present invention relates to a glass structure air filter and an aluminum honeycomb structure air filter which are manufactured by selecting a material having high light transmittance or high reflectance and gloss for a filter structure to maximize the efficient use of limited source light and thus further increase the photocatalytic activity of the air filter and improve air purification efficiency.

BACKGROUND ART

In the structure of a conventional air purifier, a pre-filter, a HEPA filter, an activated carbon filter, or a plasma ion generator or an anion generator is introduced to form a filter unit of the air purifier. Although an air purifier having such a structure is advantageous for removing dust of a certain size or ultrafine dust, in the case of an organic gas contained in the air, since the molecules which are a lot smaller than pores of the filter pass through the filter, the effect of removing the organic gas is insignificant. In a filter structure employing an activated carbon filter, although a low concentration organic gas is adsorbed, captured, and removed using the cage effect of the activated carbon having a porous structure, it has been found that, in the long term, the captured organic gas is liberated due to the adsorption capacity, wind, and temperature of the activated carbon filter. Recently, in order to compensate for the organic gas removal problem, products in which a photocatalyst-coated filter is used alone or in addition to the above-described filters have been developed. However, when evaluating organic gas decomposition performance, some photocatalytic air filters do not meet customer expectations.

In general, in the case of an air purifier employing a photocatalyst-coated air filter, the selection of a material to which the photocatalytic coating is applied is important. For the purpose of improving organic gas decomposition by the photocatalyst, various types of photocatalyst-coated filter materials are used.

A U.S. air purifier company configured an air filter using a photocatalyst-coated glass material which is a glass tube cut to a predetermined length, but in this case, since the glass tubes were randomly filled in a case without having a particular directionality, it was found that the speed of wind flow was negatively affected, and since the wind speed was not high enough, the efficiency of organic gas removal was not high.

A Korean company is marketing an air filter manufactured by Russian technology which has a structure of bonded glass beads having a photocatalytic coating on the surface, but since the air filter structure is arranged parallel to a wind flow direction, the contact time of polluted air with the photocatalyst-coated glass bead material is short, and since a photocatalytic air purifier using natural convection of air by heat is configured, wind speed is very low, so the photocatalytic effect is far below expectations.

An air purifier having a photocatalytic filter structure with increased efficiency disclosed in Korean Laid-Open Patent Application No. 10-2016-0098631 employs an air filter including a ceramic honeycomb filter coated with a photocatalyst. However, since the ceramic filter having a porous membrane has light-absorbing characteristics and the intensity of light rapidly decreases after traveling a certain distance, the effective height of the photocatalytic-filter is limited to 30 mm or less. Due to this problem, the available capacity is somewhat limited to sufficiently treat a large amount of organic gas, so it is used only for small-sized air purifiers. Also, since the porous structure of the ceramic filter itself tends to absorb an undecomposed organic gas, there is a possibility that the filter itself may cause an unpleasant smell.

DISCLOSURE

Technical Problem

The present invention is directed to providing a photocatalytic air filter for an air purifier, which does not significantly impede air flow, maximizes the intrinsic organic gas decomposition efficiency of the photocatalyst, has improved durability and a maximized photocatalyst coating area within the air filter due to the enhanced adhesion between the photocatalyst and a material to which the photocatalytic coating is applied, is manufactured by selecting a material having high light transmittance or reflectance for the efficient use of source light and optimized in consideration of the fact that it is advantageous to use a filter material that does not have a porous structure capable of adsorbing an organic material.

The present invention is directed to maximizing the above-described photocatalytic decomposition efficiency, by maximizing a photocatalyst coating area, facilitating air flow, improving a source light efficiency degradation problem caused by opaque and non-reflective characteristics (surface with low reflectance), and selecting a glass material having high transmittance and an aluminum metal material having high reflectance and gloss as materials for forming a filter structure in manufacturing a photocatalyst-coated air filter coated by primarily considering the unpleasant smell problem caused by the porosity of a material to which a photocatalytic coating is applied, thereby further improving the efficiency of source light, improving photocatalytic activity as much as possible, and further improving air purification efficiency. In addition, when applying a photocatalytic coating to a metal substrate, there is a difficulty in applying the photocatalyst due to the water repellency of a metal surface. When a large amount of binder is used to enhance the bonding between the photocatalyst and the substrate, the photocatalytic effect is significantly reduced, and when a binder is not used or a small amount of binder is used, a formed film is easily lost because of the weak bonding between the substrate and the photocatalyst, so it is necessary to develop a method to improve these problems.

In the present invention, the adhesion between the photocatalyst and the substrate can be improved by introducing and forming a photocatalytic precoat layer that can serve as a bridge (connecting layer) when applying the photocatalyst to the metal surface. In addition, the photocatalyst-coated glass structure air filter and aluminum honeycomb structure air filter installed inside the air purifier show organic gas decomposition and sterilization effects when optically activated by the light supplied from a light source, and using these effects, it is possible to provide a photocatalytic air filter structure with an improved effect of improving a polluted environment.

Technical Solution

One aspect of the present invention provides an air purification filter system, which is constructed by selecting a colloidal photocatalytic precoat solution, a photocatalytic topcoat sol solution, a glass material having excellent light transmittance or an aluminum metal material having high reflectance and gloss and configured with an air filter structure coated with double photocatalytic layers and an ultraviolet (UV) light-emitting diode (LED) lamp as a light source.

The photocatalytic topcoat sol solution preferably includes, as a photocatalyst, titanium dioxide alone or a composite catalyst formed of titanium dioxide and $WO_3$, $ZnO$, $SnO_2$, $CdS$, or $ZrO_2$, or $TiO_{(2-x)}N_x$ which is titanium dioxide doped with nitrogen.

In addition, the photocatalytic sol solution is a colloidal sol solution suitable for a purpose prepared by obtaining a solution by hydrolyzing a photocatalyst precursor at low temperature, subjecting the solution to a solvothermal reaction and thus obtaining a crystallized titanium dioxide sol solution, and post-treating the crystallized titanium dioxide sol solution, and it is particularly preferable to achieve bonding with a substrate by applying a colloidal photocatalytic precoat, rather than additionally using a binder, and performing sintering at high temperature.

In addition, a light source having a wavelength of 385 nut or less is used with a titanium dioxide-based photocatalyst, and it is preferable to select a glass material having high light transmittance in the UVA region (320 to 380 nm).

In addition, in the case of the above-described glass structure air filter having excellent transmittance, by predicting a photocatalyst-coated surface area and air resistance for a photocatalytic glass structure air filter manufactured using a material with excellent light transmittance, such as a glass plate and/or a glass tube, and a photocatalytic aluminum honeycomb structure air filter having a surface with high reflectance and gloss by using a geometric surface area (GSA; units: $m^2/m^3$) value, which is an area that can be coated with photocatalyst calculated per unit volume, and an open frontal area (OFA; units: %) value, which is a ratio of air passing through a front surface to air coming into contact with the surface, it is possible to manufacture a more effective photocatalytic air filter.

Another aspect of the present invention provides a method of manufacturing an air filter in which a glass substrate and/or aluminum metal substrate to which a colloidal photocatalytic precoat is applied is coated with a photocatalyst.

In the photocatalytic air filter of the present invention for obtaining an efficient photocatalytic oxidation reaction effective for a system for removing and treating organic gas compounds including formaldehyde which is a representative volatile organic compound (VOC) generated in an indoor environment, since an insulating coating layer is formed by introducing a photocatalytic precoat to a surface of a substrate, the adhesion between the substrate surface and a photocatalytic layer is improved and a problem in which the performance of the photocatalytic oxidation reaction is reduced due to electron leakage due to electron transfer to an aluminum metal surface is solved. The effect of the photocatalytic oxidation reaction is as follows. When UV rays with a wavelength of 385 nm or less are absorbed, electrons ($e^-$) are moved due to band gap energy difference, and electron holes (which form hydroxyl radicals ($^.OH$)) are formed on the surface of the photocatalyst particles, and when a material to be decomposed is adsorbed while passing through a surface of an air filter formed of a predetermined photocatalytic membrane, the material is decomposed by the strong oxidizing power of hydroxyl radicals formed by the electron holes.

Although in a conventional air purification device to which a photocatalyst was applied, a binder was used to attach the photocatalyst to a surface of the air filter structure to realize the effect of photocatalytic oxidation reaction, in this case, there was a problem in that since the particle surface was covered with the binder component, the formation of electron holes was inhibited and the effect was reduced.

In addition, since the photocatalytic oxidation reaction is a surface reaction, in order to effectively remove VOCs or odorous substances, it is necessary to increase the surface area of a particle layer coming into contact with these substances or increase the intensity and amount of UV light. Accordingly, there is a need to develop a system configured of a structure capable of efficiently providing a large surface area and photocatalytic activity.

Therefore, in the present invention, a colloidal photocatalytic precoat was developed so that an air filter with excellent bonding strength and high photocatalytic activity can be applied to an air purifier, and an air purification filter system capable of efficiently decomposing and removing harmful environmental substances such as formaldehyde was completed.

In particular, in the photocatalytic air filter, in the case of a glass substrate, in order to apply a colloidal photocatalytic precoat and a photocatalytic topcoat to the glass material, it is preferable to form a structure by uniformly applying a photocatalytic sol solution to the glass material by one or more coating methods such as a spray-coating method, a flow-coating method, and a dip-coating method, and in the case of an aluminum honeycomb structure, since the structure has a dense cell structure, it is preferable to apply surface coating by the dip-coating method.

In particular, the coating operation for forming the photocatalytic topcoat layer is not limited to one time, and applying a low-concentration photocatalyst several times is advantageous for improving the bonding between the photocatalyst and the substrate, and when applying a coating, it is preferable to perform heat-drying at 120 to 150° C. for 20 to 30 minutes after applying each coating to induce the formation of a dense pre-coating film structure.

In particular, it is preferable to subject the photocatalyst-coated substrate to sintering for 30 minutes to 2 hours at 400 to 550° C. so that the adhesion between the topcoat layer, the precoat layer, and the substrate surface can be further enhanced. In this case, in the case of performing sintering at high temperature for a long time, although the adhesion may be improved, the structure of the titanium dioxide photocatalyst may be converted from an anatase form to a rutile form, causing photocatalyst efficiency to be significantly reduced, so there is a need for research to optimize the sintering temperature and time.

In addition, a photocatalyst-coated glass material should be assembled to a predetermined size and used, and in this case, for the efficient utilization of UV light, it is advantageous in terms of light efficiency to use a material having light-reflective characteristics, such as a mirror, as an outer material surrounding the glass material.

Advantageous Effects

A glass structure air filter and an aluminum honeycomb structure air filter to which a colloidal photocatalytic, precoat and a photocatalytic topcoat designed in the present invention are applied have excellent durability due to the enhanced adhesion between the photocatalyst and a substrate surface and realize superior performance compared to existing products in terms of organic gas decomposition by a photocatalyst. That is, a photocatalytic air filter having a significantly higher organic gas removal efficiency than a general HEPA filter or a filter type including an activated carbon filter in addition to a HEPA filter is provided.

In addition, the above-described air filters have more efficient organic gas removal performance even compared to ceramic filters.

Using the above-described ability to remove an organic gas and especially the excellent ability to remove formaldehyde, it is possible to improve the living environment of people suffering from atopic diseases caused by chemicals, improve sick house syndrome and new car syndrome, and efficiently remove an unpleasant smell generated in food storage, refrigerators, and the like. In addition, when the air filters of the present invention are enlarged, they can be used for efficiently removing an organic gas generated in laboratories, industries, and the like.

BEST MODE

Figure 3:
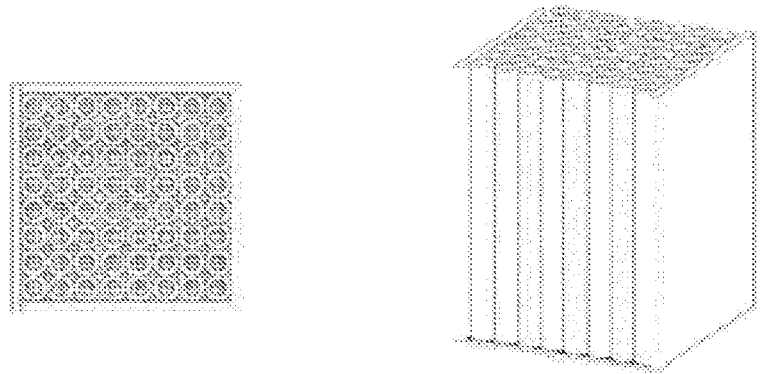
FIG. 3 shows a cross-sectional view and a perspective view of a photocatalytic glass tube structure air filter according to one exemplary embodiment of the present invention.
Figure 4:
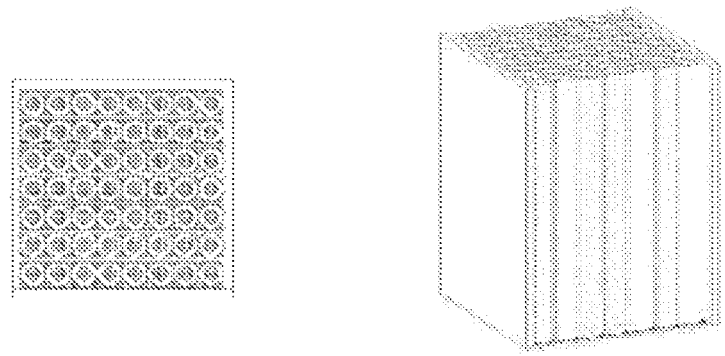
FIG. 4 shows a cross-sectional view and a perspective view of a photocatalytic glass plate/glass tube structure air filter according to one exemplary embodiment of the present invention.
Figure 5:
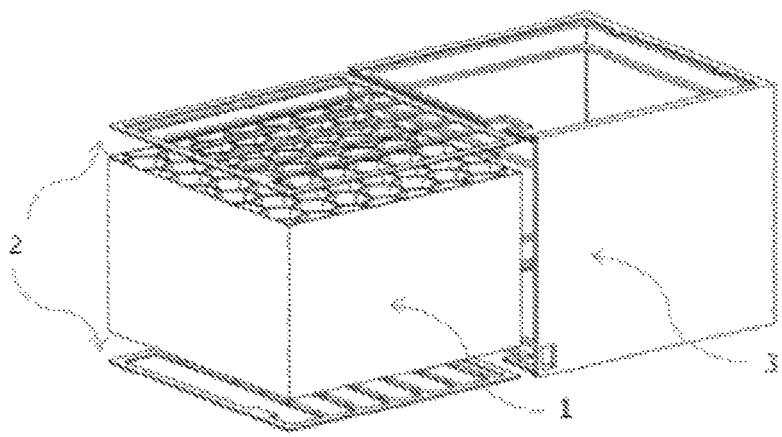
FIG. 5 is a layout view of UVA-LED printed circuit boards (PCBs) and a photocatalytic aluminum honeycomb structure air filter.

FIGS. 1 to 5 illustrate the structures of various air filters according to exemplary embodiments of the present invention, representative of which is a structure of FIG. 5 configured of a photocatalytic aluminum honeycomb structure 1, UVA-LED PCBs 2, and a photocatalytic-filter module housing 3.

The following is a brief description of a method of preparing a photocatalytic topcoat used in the present invention.

First, titanium tetraisopropoxide (TTIP) with a purity of 98% is added to anhydrous ethanol, and a small amount of water and tetraalkyl ammonium hydroxide (TAAH) are added to induce hydrolysis, and the hydrolysis is slowly carried out at room temperature for six hours. The obtained solution is input in a high-pressure reactor and tightly sealed to prevent leakage of the solvent, and then a solvothermal method is carried out in a high-temperature and high-pressure atmosphere, that is, at a temperature of 250° C., for six hours, and thereby a titanium dioxide crystal phase having an anatase structure is obtained in a solution form. When the obtained solution is washed several times by centrifugation using ethanol to remove the TAAH used in the reaction and made into an acidic solution having a pH of 1 to 2 by using a strong acid solution, a colloidal dispersion solution in which ultrafine particles are very well dispersed is obtained. The content of titanium dioxide obtained in this case is about 10 to 20 wt %. The obtained colloidal photocatalyst solution is preferably diluted to a concentration suitable for application to a spraying method or a dip-coating method and used. This is because when the concentration is excessively high, there is a high risk of delamination during the coating process, and on the other hand, when the concentration is excessively low, an increased number of coatings should be performed, which takes a lot of time. Therefore, it is also necessary to select an appropriate concentration. Since the diluted titanium dioxide sol solution does not contain a binder, sintering should be performed at high temperature to impart bonding strength.

In particular, to enhance the bonding between a substrate surface and a photocatalytic layer forming a topcoat, a colloidal photocatalytic precoat is applied therebetween in the present invention. After preparing a mixture of a siloxane reactant having excellent adhesion to a ceramic material (e.g., glass) and a metal material and the above-described titanium dioxide sol solution and forming a precoat layer and a photocatalytic topcoat layer on a suitable substrate capable of withstanding high temperatures, sintering is carried out at a high temperature of 400° C. to 550° C. so that the titanium dioxide compound forms a stable anatase structure, and at the same time, the bonding between the photocatalyst and the substrate can be enhanced at high temperature.

In the present invention, the selection of a material to which a photocatalyst coating is applied is very important. A usable material may be selected from among metal materials, ceramic materials, and the like because the material should not be carbonized or deformed during the high-temperature sintering process, but it should be considered that when a metal material is selected, electrons generated in a photocatalytic reaction may leak, and the material may be degraded and deformed at high temperature. For example, well-known honeycomb ceramic filter materials have an economical aspect when considering the price, but in terms of performance, UV light is absorbed at a surface of the material, and when a honeycomb ceramic filter material having a compact cell size is used in order to increase the effective surface area of a photocatalytic layer, there are problems in that UV light is blocked by partition walls and resistance to air flow occurs, so the efficient use of a photocatalytic oxidation reaction is inhibited. In addition, in terms of the intensity of UV light, as the air flow path length of a filter increases, the intensity of light reaching the surface of a pipe center and an irradiation area decrease. Therefore, as the height of the ceramic honeycomb filter increases, efficiency decreases.

Therefore, in the present invention, based on experimental results obtained through preliminary experiments, by using a glass material with excellent light transmittance but very low light absorption and an aluminum metal material with high reflectance and gloss, light supplied from a light source can be used after intensity optimization. For example, a ceramic filter has remarkably excellent organic gas decomposition performance when having a thickness of 3 cm to 5 cm as compared to when having a height of 10 cm. However, when a substrate of the present invention is used, since light is hardly absorbed, a photocatalytic effect is realized even with a height of 20 cm or more, and in one exemplary embodiment of the present invention, the effect is realized with an optimized height of 15 cm.

Types of commercially available glass materials can be divided into plate-shaped types and glass-tube types. The size of a material to be used is selected through a preliminary experiment carried out for material selection.

In the case of glass plates, there are many types of glass plates with different thicknesses. When installing the glass plates in a limited space, the number of glass plates that can be installed depends on die thickness, quantity, and spacing between the glass plates, and the photocatalyst coating area is proportional to the total number of installed glass plates.

In a preliminary experiment of the present invention, it was found that when thick glass was used, the photocatalyst coating area was reduced and organic gas decomposition performance was proportionally affected, and it was confirmed that the most efficient glass thickness was 0.3 mm to 0.5 mm in terms of increasing a surface area.

In particular, in the case of glass tubes, glass tubes of various sizes were provided and tested, and it can be seen that the smaller the size of the glass tube, the higher the spatial density and the lower the wind speed and air volume, and thus the smaller the photocatalytic, decomposition effect, and on the other hand, when the size of the glass tube was excessively large, although wind speed and air volume increased, a photocatalyst coating area was reduced, and a photocatalytic decomposition effect was again reduced. The configuration of the glass tube having effective performance had an inner diameter of 2 mm to 3 mm and an outer diameter of 4 mm to 5 mm, and in this case, VOC removal efficiency was the highest.

In order to realize organic gas decomposition by a photocatalyst, it is essential to install an air filter in which a photocatalytic layer is formed on a colloidal photocatalytic precoat layer within a structure configured to have a size in accordance with a specific standard and supply light in the UV region using a light source.

In general, since the hand gap energy of titanium dioxide ($TiO_2$) is 3.2 eV, the threshold energy for the activation of a titanium dioxide-based photocatalyst should be less than 385 nm. That is, it is preferable to use a source light in the UVA region (320 nm to 380 nm), which is a relatively safe UV region, as a source light for imparting photochemical activity to the photocatalyst.

The UVA lamps that are currently most commonly used have a large size, and the intensity of the supplied light per unit area is only a few $mW/cm^2$. However, the recently developed UVA LED light sources are small and have a size of only a few millimeters, and since the intensity of emitted light of a specific wavelength is very strong as compared to the lamp type and several tens of $mW/cm^2$, the UVA LEDs have a number of advantages when used in a small space, such as in the case of small appliances, and in terms of a lifespan, the replacement cycle of the UVA LEDs is very long and 25,000 hours or more whereas the general replacement cycle of the lamp type is 3,000 to 4,000 hours, so the UVA LEDs are easy to maintain. Disadvantages are that since the UV A LEDs are expensive, there is a limitation on increasing the number of LEDs used, and the generation of heat, which is a characteristic of LEDs, damages a circuit and shortens its lifespan, so measures against heat are absolutely necessary in devices employing the LEDs.

Factors affecting the photocatalyst-coated air filters used in air purifiers include the intensity of supplied source light, the amount and area of a photocatalyst coating, the air volume of an air circulation fan, and the ambient temperature and humidity, and what is most important is the selection of a material to which the photocatalyst is applied.

In the photocatalytic-filter manufactured as described above, a photochemical photocatalytic reaction occurs due to supplied source light, and the organic compounds introduced to a photocatalyst surface undergo several chemical reaction steps, and gaseous water ($H_2O$) and carbon dioxide ($CO_2$) are generated as final products.

The mechanism of the formaldehyde gas decomposition reaction by die photocatalyst occurring in one exemplary embodiment of the present invention is known as follows.

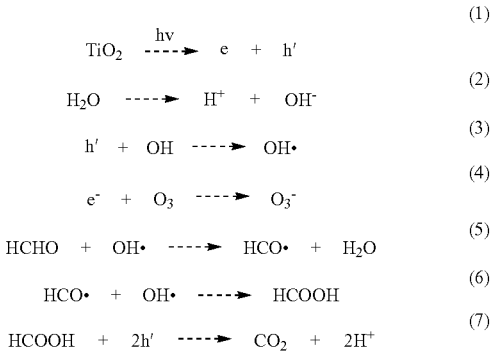

When light energy that is greater than or equal to band gap energy is applied to titanium dioxide having semiconductor characteristics, the titanium dioxide acts as a heterogeneous photocatalyst, and an organic compound adsorbed on a surface of the photocatalyst undergoes catalytic chemical decomposition. This mechanism can be briefly summarized as follows. When a metal oxide having semiconductor characteristics is irradiated with energy that is greater than or equal to the band gap energy, electrons are excited by photons and move from the valence hand to the conduction band and thus electron-deficient holes (electron holes) are formed in the valence band, and the electrons excited to the conduction band cause a chemical reaction. In addition, hydroxyl radicals ($^{\cdot}OH$), which are generated from a reaction between the formed electron holes and a hydroxyl group ($OH^-$) supplied from moisture (water) in the air, are very strong chemical species that cause oxidation, and participate in the decomposition of organic compounds through the oxidation of the organic compounds, and super oxide anions ($O_2^-$) generated in a reaction between oxygen contained in the air and the electrons excited to the conduction band are chemical species that participate in a reduction reaction, and do not participate in the decomposition of the organic compounds. The hydroxyl radicals generated as described above serve as a catalyst that continuously acts in the decomposition of the organic compounds and participates in the decomposition of the organic compounds without being consumed during the cycle. Therefore, the process of forming abundant electrons and electron holes per unit time is an important factor in the production of the photocatalytic effect.

In the present invention, it was possible to control the intensity of the air volume using a blower-type air fan, and it was found that the organic gas decomposition effect by the photocatalyst was variable and depended on the air volume.

In addition, it was found that the photocatalytic decomposition reaction, like the other general chemical reactions, was affected by temperature and humidity, and when an experimental temperature was lowered, there was a tendency that the decomposition and removal efficiency decreased as the gas diffusivity of a material to be decomposed decreased. Therefore, in order to evaluate the pure effect of photocatalyst, an organic gas decomposition experiment was conducted using formaldehyde while maintaining chamber temperature at 25±3° C. and adjusting relative humidity within 50±15%.

The following exemplary embodiments are presented to illustrate the present invention in detail, and the scope of the present invention is not limited by these exemplary embodiments.

Example 1: Preparation of Photocatalytic Topcoat Solution

A photocatalyst solution used for a topcoat was prepared by the above-described hydrothermal synthesis method, and the synthesis process of the obtained photocatalytic topcoat solution can be briefly described as follows. First, 1 kg of anhydrous ethanol having a purity of 99.5% was input into a 2 L glass beaker, and 320 g of TTIP having a purity of 98% was added over 30 minutes while stirring at room temperature. Although some heat was generated during stirring, the reaction was carried out while maintaining this state. To this, 65 g of a tetrabutylammonium hydroxide (TBAH) solution in which TBAH at 40% (w/w) was dispersed in water was added over 10 minutes. Subsequently, the solution was transferred to a high-pressure reactor and tightly sealed to prevent leakage of the solution, and then a solvothermal reaction was performed for six hours under a high-temperature and high-pressure conditions of 250° C., and thereby a titanium dioxide crystal phase having an anatase structure was obtained in a solution form. The obtained solution was washed three times by centrifugation using 2 kg of ethanol to remove the TBAH used in the reaction and thus titanium dioxide dispersed in an ethanol solvent was obtained, and the acidity thereof was adjusted to an acidic solution with a pH of 1 to 2 by using a 0.01 N nitric acid solution, so a colloidal titanium dioxide solution in which ultrafine particles were very well dispersed and which had a solid content of 8 wt % was obtained. Finally, using water and ethanol, a titanium dioxide photocatalytic topcoat solution having a solid content of 5 wt % was prepared.

Example 2: Preparation of Photocatalytic Precoat Solution

To the 60 wt % titanium dioxide (photocatalytic topcoat) sol solution obtained in Example 1 having a solid content of 8 wt %, 1.5 wt % tetraethyl orthosilicate (TEOS), 1.5 wt % methyl triethoxysilane (MTEOS), 36 wt % anhydrous ethanol (purity: 99.5%), and a 0.5 wt % 0.006 N aqueous nitric acid solution were added and reacted for two hours while raising a reaction temperature to 70° C., and then 0.5 wt % tetra-n-butyl titanate (TnBT) was added and reacted, and thus a colloidal titanium dioxide photocatalytic precoat solution was obtained.

Example 3: Manufacture of Double, Photocatalyst-Coated Glass Plate Structure Air Filter In order to prepare a photocatalyst-coated glass plate structure using the photocatalytic topcoat and photocatalytic precoat prepared in Examples 1 and 2, provided glass plates (100 mm (W)×0.3 mm (D)×150 mm (H); 100 plates) were first washed and dried, and immersed in the precoat solution prepared in Example 2 at room temperature for dip-coating, naturally dried at room temperature for at least 30 minutes, and pre-cured in a drying oven at 150° C. for 30 minutes to form a colloidal photocatalytic precoat film. Subsequently, using a dip-coating method and the photocatalytic topcoat sol solution having a solid content of 5 wt % prepared in Example 1, a predetermined photocatalytic layer was additionally formed on the surface of the photocatalytic precoat, and dried at room temperature for 30 minutes and then in a drying oven at 150° C. for 30 minutes, and then sintered for one hour in a kiln at 450° C. to enhance the bonding between the photocatalyst and the substrate. In this process, a trace amount of residual surfactant contained as an impurity was completely removed, and a coated substrate in which a photocatalytic layer is strongly bound to the surface of the substrate was obtained.

Figure 1:
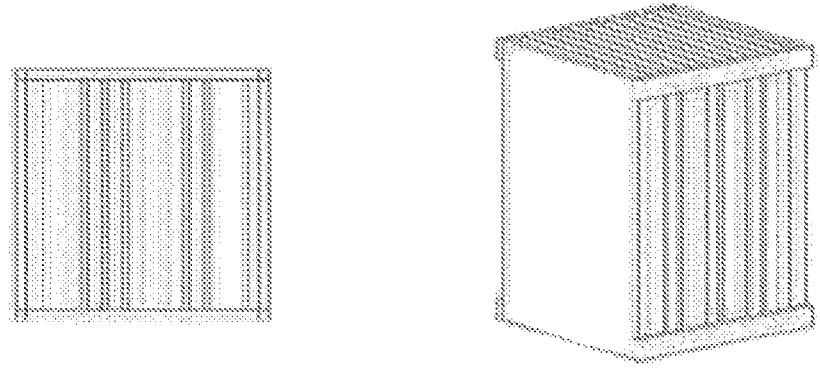
FIG. 1 shows a cross-sectional view and a perspective view of a photocatalytic glass plate structure air filter according to one exemplary embodiment of the present invention.

One hundred photocatalyst-coated glass plates thus obtained were assembled in such a manner that they were laminated at regular intervals of 0.7 mm within a structure formed with the size of 100 mm (W)×100 mm (D)×150 mm (H) using acrylic mirror plates (thickness: 3 T) capable of reflecting light, and thus a photocatalyst-coated glass plate air filter having a GSA value of 2,000, an OFA value of 69, and a photocatalytic film surface area of 3.0 $m^2$ was obtained. FIG. 1 is an exemplary cross-sectional view of the obtained photocatalytic glass filter.

Figure 2:
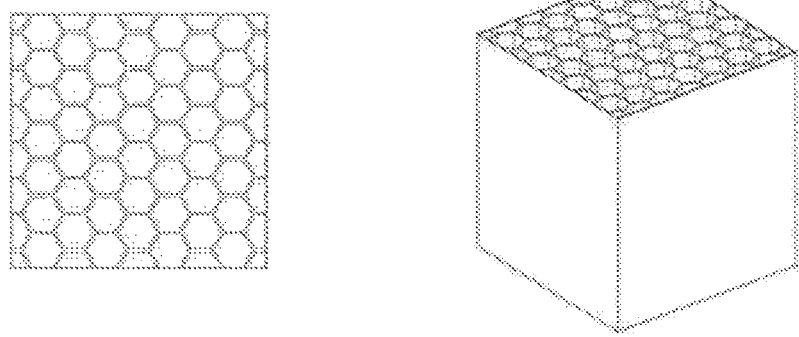
FIG. 2 shows a cross-sectional view and a perspective view of a photocatalytic aluminum honeycomb structure air filter according to one exemplary embodiment of the present invention.

Example 4: Manufacture of Air Filter Using Photocatalyst-Coated Aluminum Honeycomb Structure An aluminum honeycomb structure (107 cells per square inch (CPSI); size: 100 mm (W)×100 mm (D)×150 mm (H)) was washed and dried, and a precoat layer and a topcoat layer were applied in the same manner as in Example 3, and thus an aluminum honeycomb structure air filter in which the bonding between the aluminum metal substrate and the photocatalytic coating was enhanced was obtained, and a GSA value calculated therefrom was 1,490, an OFA value was 96, and a photocatalytic membrane surface area was 2.2 m². FIG. 2 is an exemplary cross-sectional view of the obtained photocatalytic aluminum honeycomb structure air filter.

Example 5: Manufacture of Photocatalyst-Coated Glass Tube Structure Air Filter Glass tubes having an outer diameter of 4 mm, an inner diameter of 2.4 mm, and a length of 150 mm were provided and used. A photocatalytic precoat layer and a photocatalytic topcoat layer were formed in the same manner as in Example 3.

In laminating the obtained photocatalyst-coated glass tubes in the internal space of a structure formed with the size of 100 mm (W)×100 mm (D)×150 mm (H) using acrylic mirror plates (thickness: 3 mm), the glass tubes were arranged in rows so that they were only perpendicular to the floor to have as little wind resistance as possible, and thus a photocatalyst-coated glass tube air filter having a GSA value of 1,260, an OFA value of 49, and a photocatalytic film surface area of 1.8 m² was obtained. FIG. 3 is a cross-sectional view of the obtained photocatalytic glass tube structure filter.

Example 6: Manufacture of Air Filter Using Photocatalyst-Coated. Glass Plates and Glass Tubes Glass plates of the same size as the glass plates used in Example 3 were provided and used, and glass tubes having an outer diameter of 5 mm, an inner diameter of 3.4 mm, and a length of 150 mm were provided.

A photocatalyst was applied to the glass plates and glass tubes using the method performed in Example 3, and thereby photocatalyst-coated glass tubes and glass plates were obtained.

The obtained photocatalyst-coated glass tubes and glass plates were arranged, in the internal space of a structure formed with the size of 100 mm (W)×100 min (D)×150 mm (H) using acrylic mirror plates (thickness: 3 mm), in such a manner that a row of glass tubes was placed and then a glass plate was placed, and another row of glass tubes was placed and then another glass plate was placed, and thus a photocatalytic air filter formed of glass tubes and glass plates and having a GSA value of 1,310, an OFA value of 44, and a photocatalytic film surface area of 1.9 m² was obtained. FIG. 4 is an exemplary cross-sectional view of the obtained photocatalytic glass air filter.

Example 7: Manufacture of Air Filter Using Photocatalyst-Coated Aluminum Honeycomb Structure without Photocatalytic Precoat Layer Only using the photocatalytic topcoat solution prepared in Example 1 and an aluminum honeycomb structure (107 CPSI; size: 100 mm (W)×100 mm (D)×150 mm (H)), a photocatalytic aluminum structure air filter in which only the photocatalytic topcoat layer is formed was manufactured by the above-described method, and the air filter had a GSA value of 1,490, an OFA value of 96, and a photocatalytic film surface area of 2.2 m².

Configuration of Organic Gas Decomposition Ability Measuring Device

In order to evaluate the organic gas decomposition ability of the photocatalyst-coated glass air filters manufactured in the above-described Examples, the following experimental apparatus was constructed.

The configuration of the experimental apparatus is as follows. The apparatus was made of glass to have a size of 650 mm (W)×650 mm (D)×815 mm (H) and an internal volume of 330 liters, and a formaldehyde concentration measuring device was installed inside. A blower-type fan capable of generating an air volume of 65 cubic feet per minute (CFM), that is, 110 m³ per hour, was installed to facilitate the internal air flow, and internal air circulation was allowed to occur 5.5 times per minute, and a photocatalyst-coated air filter was placed on the blower-type fan. Above and below the air filter structure, UVA LEDs which were aligned in mutually intersecting directions were inserted and installed at a distance of 15 mm from the air filter structure and used as a light source.

As the UVA LEDs, Seoul Viosys' UVA LED Z5 series lamps emitting a specific wavelength of 365 nm and having a wide viewing angle of 120° were used, and a power source operating at a direct current voltage of 16 V or less and a current of 0.35 mA or less was used.

Each of the upper and lower UVA LEDs was configured of 16 LEDs, and the distance between electrodes was 25 mm. The intensity of the UVA LED light sources was adjusted so that when measured using a UVR-2 UV radiometer manufactured by Topcon Technohouse Corporation (Japan), that is, when measured from a distance that the light emitted from the UVA LED could reach a front surface part of the air filter, the average UV intensity per unit area was 60 mW/cm², and power was supplied from the outside. FIG. 5 illustrates one installation example of a photocatalyst-coated aluminum honeycomb structure and PCBs having UVA LEDs.

Experimental Example 1: Measurement of Formaldehyde Decomposition Performance of Glass Plate Structure Air Filter In Experimental Example 1, formaldehyde gas, which is an organic gas that is a major cause of sick house syndrome and defined as a class one carcinogen and frequently generated from building materials, was used, and the rate of formaldehyde decomposition by a photocatalyst was measured.

Figure 6:
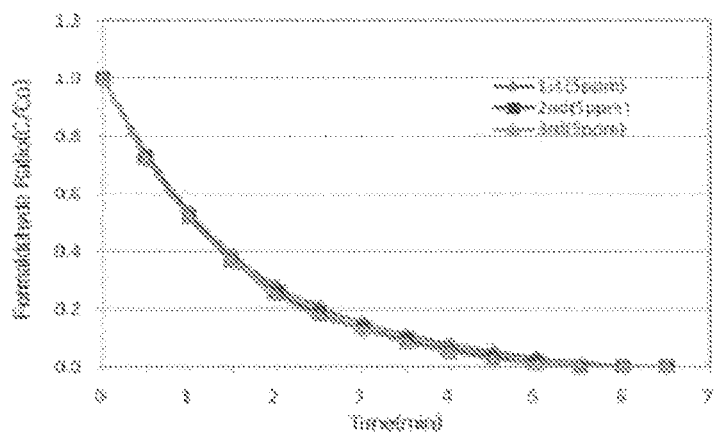
FIG. 6 is a graph showing the formaldehyde decomposition performance measured in Experimental Example 1.

First, the glass plate structure air filter prepared in Example 3 was mounted on a blower-type fan, and formaldehyde gas collected from a 40% aqueous formaldehyde solution was injected while the power of the UVA LED lamps was off and only the fan was operated so that the initial formaldehyde concentration was in the range of 5.5 to 6.0 ppm. It was confirmed that a concentration change for 10 minutes after injection of the formaldehyde gas was maintained within 1%. That is, it can be interpreted that under the conditions where the photocatalytic effect does not apply, the formaldehyde concentration changed with negligible deviation with the lapse of time. After confirming that the formaldehyde concentration was maintained within a certain range, a photocatalytic, reaction was initiated by supplying power to the UVA LEDs, and after supplying power to the UVA LEDs, measurements were taken every 30 seconds from the time when it was determined that the photocatalyst action occurred smoothly, that is, the time when the formaldehyde concentration reached 5 ppm, to the time when the concentration reached 0 ppm, and the experimental results obtained from three measurements are shown in FIG. 6. Here, in a formaldehyde ratio ($C/C_o$), C is a concentration at time t, and $C_o$ is a concentration at time to, that is, when the formaldehyde concentration is 5 ppm, and is referred to as an initial concentration. The formaldehyde removal by the photocatalyst took an average of 340 seconds.

Figure 7:
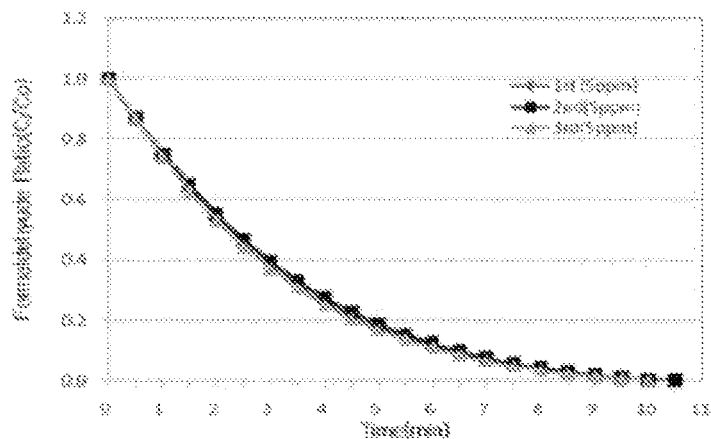
FIG. 7 is a graph showing the formaldehyde decomposition performance measured in Experimental Example 2.

Experimental Example 2: Measurement of Formaldehyde Decomposition Performance of Photocatalytic Aluminum Honeycomb Structure Air Filter The air filter configured of a photocatalytic aluminum honeycomb structure formed in Example 4 was mounted on a blower-type fan, and an experiment was performed in the same manner as in Experimental Example 1. A decomposition rate was measured at intervals of 30 seconds, and the experimental results obtained from three measurements are shown in FIG. 7. The formaldehyde removal by the photocatalyst took an average of 600 seconds.

Figure 8:
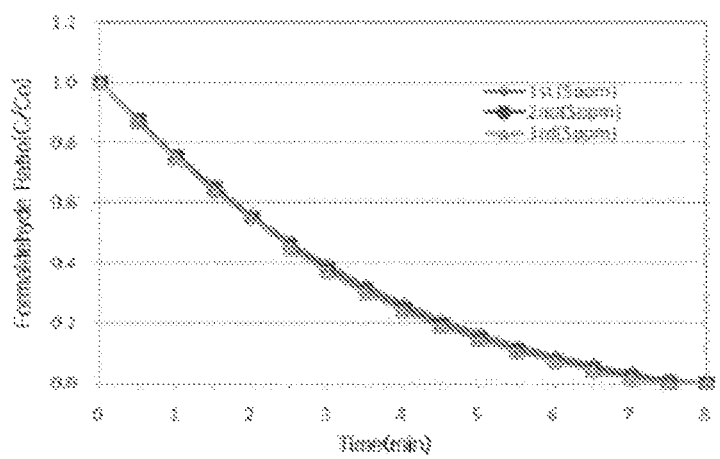
FIG. 8 is a graph showing the formaldehyde decomposition performance measured in Experimental Example 3.

Experimental Example 3: Measurement of Formaldehyde Decomposition Performance of Photocatalytic Glass Tube Structure Air Filter The glass air filter manufactured using glass tubes in Example 5 was mounted on a blower-type fan, and an experiment was performed in the same manner as in Experimental Example 1. A decomposition rate was measured at intervals of 30 seconds, and the experimental results obtained from three measurements are shown in FIG. 8. The formaldehyde removal by the photocatalyst took an average of 460 seconds.

Figure 9:
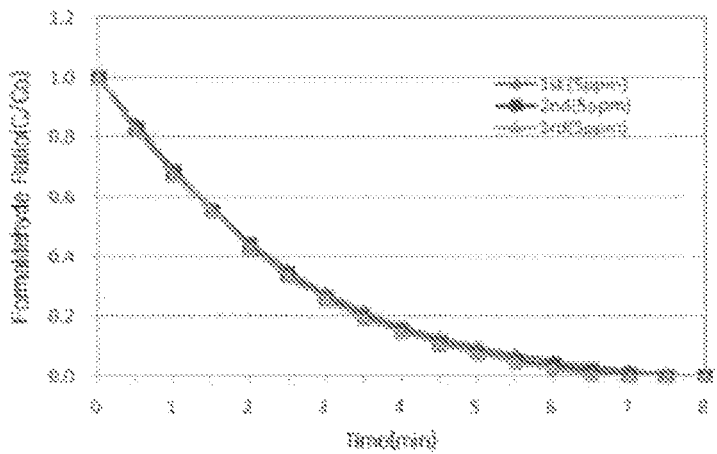
FIG. 9 is a graph showing the formaldehyde decomposition performance measured in Experimental Example 4.

Experimental Example 4: Measurement of Formaldehyde Decomposition Performance of Air Filter Configured of Photocatalytic Glass Plates and Glass Tubes The photocatalytic glass air filter manufactured using glass plates and glass tubes in Example 6 were mounted on a blower-type fan, and an experiment was performed in the same manner as in Experimental Example 1. A decomposition rate was measured at intervals of 30 seconds, and the experimental results obtained from three measurements are shown in FIG. 9. The formaldehyde removal by the photocatalyst took an average of 440 seconds.

Figure 10:
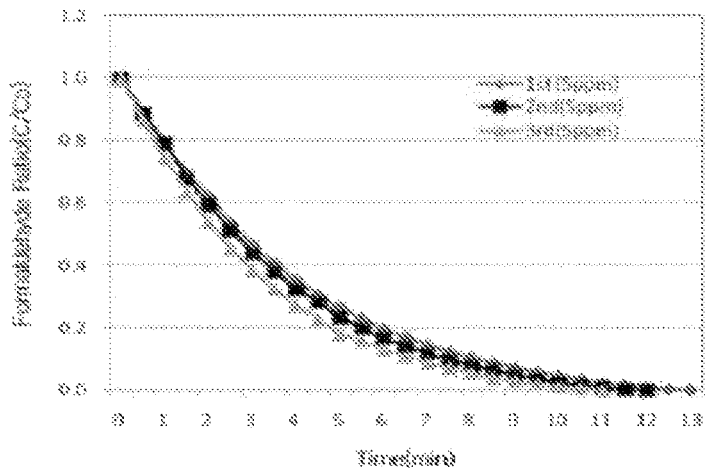
FIG. 10 is a graph showing the formaldehyde decomposition performance measured in Experimental Example 5.

Experimental Example 5: Measurement of Formaldehyde Decomposition Performance of Photocatalytic Aluminum Honeycomb Structure Air Filter without Precoat Layer The photocatalytic topcoat-coated aluminum honeycomb structure air filter without a photocatalytic precoat manufactured in Example 7 was mounted on a blower-type fan, and an experiment was performed in the same manner as in Experimental Example 1. A decomposition rate was measured at intervals of 30 seconds, and the experimental results obtained from three measurements are shown in FIG. 10. The formaldehyde removal by the photocatalyst took an average of 710 seconds.

Figure 11:
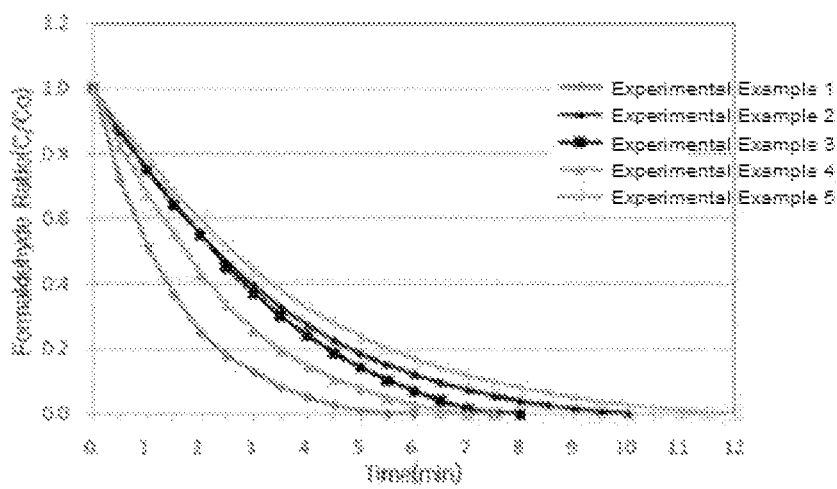
FIG. 11 is a graph comparing the formaldehyde decomposition performance of air filters according to structure types.

In order to compare the performance of the various air filter structures of Experimental Examples 1 to 5, the average formaldehyde decomposition times measured in the Experimental Examples are shown in FIG. 11. In addition, in order to analyze the characteristics of the various photocatalytic structures, the characteristics of the structures are summarized in Table 1.

TABLE 1

| Experiments | Structure materials | GSA ($m^2/m^3$) | OFA (%) | Photo-catalytic coating layer | Formaldehyde decomposition time (seconds) |
|---|---|---|---|---|---|
| Experimental Example 1 | Glass plates | 2,000 | 69 | Precoat, topcoat | 340 |
| Experimental Example 2 | Aluminum honeycomb | 1,490 | 96 | Precoat, topcoat | 600 |
| Experimental Example 3 | Glass tubes | 1,260 | 49 | Precoat, topcoat | 460 |
| Experimental Example 4 | Glass plates, glass tubes | 1,310 | 44 | Precoat, topcoat | 440 |
| Experimental Example 5 | Aluminum honeycomb | 1,490 | 96 | Topcoat | 710 |

First, when the formaldehyde decomposition rates of the glass structures are compared, it can be seen that the decomposition rates are improved in proportion to an available photocatalyst coating area per unit volume as shown in Table 1. Therefore, it can be said that the photocatalyst coating area absolutely contributes to the formaldehyde organic gas decomposition rates.

In addition, in the case of the glass tube structure air filter (Comparison of Experimental Examples 1, 3 and 4), it can be confirmed, from the above experiment, that the dependence of the organic gas decomposition rate on the OFA value is opposite to the tendency that the larger the photocatalytic coating surface area, the faster the decomposition. Considering the fact that it can be predicted that the lower the OFA value, the higher the probability of contact between organic gas particles diffused in the air and the photocatalyst particle surface, it can be interpreted that a photocatalytic reaction, which is a cycle of organic gas adsorption and oxidative decomposition, produces relatively good organic gas decomposition results. Since these test results are closely related to the air circulation by an air purifier and the purification ability according to the decomposition of an organic gas, the OFA value can be considered as an important factor in the actual design of an air purifier filter.

In addition, when a glass plate structure and an aluminum honeycomb structure are compared, the photocatalyst coating area of a glass plate structure is about 1.34 times larger than that of an aluminum honeycomb structure of the same volume, and considering this fact and inferring decomposition rates by assuming the same photocatalyst area, the decomposition time by an aluminum structure is expected to be about 450 seconds. However, a decomposition time measured in actual experiments is longer, for the following reasons. While it can be expected that the source light incident on the glass plates will contribute to photocatalytic activation through transmission and reflection, in the case of the aluminum structure, since the substrate does not inherently transmit light, the use of light depends only on reflective characteristics, and thus, the efficiency of using light is lower than that of the glass materials. It can be inferred that the same results will be obtained when the aluminum structure is compared with Experimental Examples 3 and 4.

In addition, according to the results of studying aluminum structures, Example 2 had significantly excellent properties as compared to Example 5. It can be interpreted that the electron leakage phenomenon of a metal material is responsible for the decomposition rate difference under the same photocatalyst surface area, light source, and air volume conditions. That is, in the manufacture of a photocatalyst structure, a photocatalytic topcoat was applied after forming an insulating film using a precoat layer in Experimental Example 2, and only a photocatalytic topcoat was used in Experimental Example 5. It is interpreted that, since the structure of Experimental. Example 2 in which an insulating film was formed can more effectively block the electron movement to a metal surface than Experimental Example 5, more abundant electrons can be present in the photocatalyst surface layer, and thus the decomposition effect is improved. This means that when forming a photocatalytic layer using a metal material, it is preferable to form an insulating film using a precoat material for higher efficiency. In addition, when the surfaces of photocatalytic layers were rubbed with wool (felt), structures including a photocatalytic topcoat had a higher risk of delamination, whereas photocatalytic structures including a precoat layer had much superior adhesive strength and high durability that they only had scratches.

Comparative Example 1: Measurement of Formaldehyde Decomposition Performance of True HEPA Filter (Class H13) Air Purifier In Comparative Example 1, a commercially available air purifier including a class H13 HEPA filter was purchased, and formaldehyde decomposition performance according to time was measured. A cylindrical HEPA filter having a height and diameter of 17 cm and a corrugated HEPA filter having a thickness of about 2 cm were used.

Figure 12:
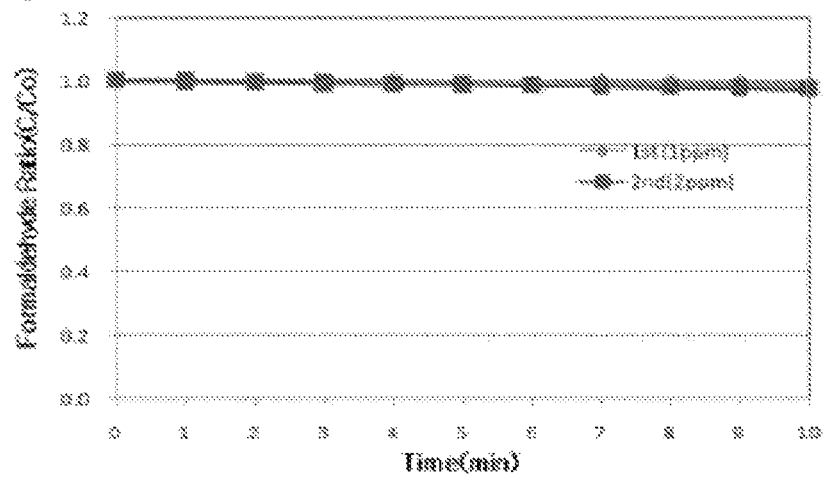
FIG. 12 is a graph showing the formaldehyde decomposition performance measured in Comparative Example 1.

In a first experiment, formaldehyde was injected at a concentration of 1 ppm, and formaldehyde gas concentration according to time was measured. However, the gas adsorption level of the HEPA filter for 10 minutes was insignificant and was about 1.%. In a second experiment, the above-described experiment was conducted again with an increased concentration of 2 ppm, but considering the fact that the reduction of formaldehyde was within an error range as shown in FIG. 12, the effect of removing formaldehyde by the true HEPA filter was negligible. This is because the molecular size of formaldehyde was a lot smaller than pores of the HEPA filter so the filtration or adsorption of the organic gas hardly occurred. Therefore, the HEPA filter is not suitable for removing formaldehyde gas.

Comparative Example 2: Measurement of Formaldehyde Decomposition Performance of Air Purifier Including HEPA Filter and Activated Carbon Filter In Comparative Example 2, a commercially available air purifier including a cylindrical HEPA filter and an active carbon filter was purchased, and formaldehyde decomposition performance according to time was measured.

Figure 13:
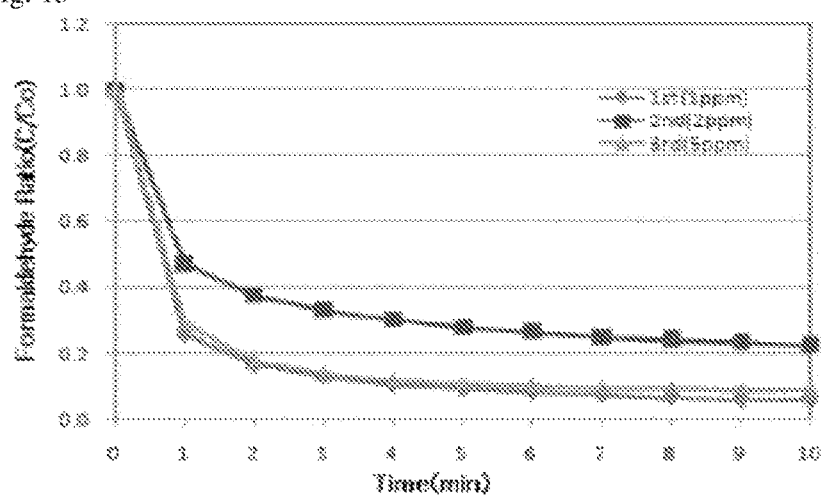
FIG. 13 is a graph showing the formaldehyde decomposition performance measured in Comparative Example 2.

In a first experiment, formaldehyde was injected at a concentration of 1.5 ppm, and a rate of formaldehyde removal according to time was measured from the time point at which a concentration of 1.0 ppm was reached. In a second experiment, 2.5 ppm was injected, and a rate of formaldehyde removal according to time was measured from the time point at which a concentration of 2.0 ppm was reached. In a third experiment, 6 ppm was injected and a rate of formaldehyde removal according to time was measured from the time point at which a concentration of 5 ppm was reached. Considering that the effect of removing formaldehyde by the HEPA filter in Comparative Example 1 was insignificant, it can be concluded that the reduction in formaldehyde concentration observed in the three experiments is an effect due to adsorption by activated carbon. The organic gas adsorption by the activated carbon was found to be very effective at the beginning. However, contrary to expectations, it was observed that the adsorption performance was very poor over time and thus did not significantly affect the removal of residual formaldehyde. In addition, as the experiments were repeated, the concentrations of formaldehyde at 10 minutes after the start of the experiments were 0.06 ppm in the first experiment, 0.33 ppm in the second experiment, and 0.46 ppm in the third experiment, showing a significant increase in the residual concentration value. The adsorption performance of activated carbon is related to its intrinsic organic gas adsorption amount, and considering that the adsorbed organic gas may be liberated due to wind speed or temperature, the above-described adsorption performance of activated carbon does not satisfy the expectation of the complete removal of an organic gas. That is, since the formaldehyde adsorption/removal rate by activated carbon becomes very slow after a certain time point, it is interpreted that activated carbon has a limit in continuously removing an organic gas having a small molecular weight such as formaldehyde. The experimental results are shown in FIG. 13.

Comparative Example 3: Measurement of Formaldehyde Decomposition Performance of Photocatalyst-Coated Ceramic Filter In Comparative Example 3, a coating was applied in the same manner as in Example 3 to a honeycomb structure ceramic filter formed of cordierite, and then formaldehyde decomposition performance was measured under the same experimental conditions as in Experimental Example 1. The ceramic filter used in this case had a cell density of 200 CPSI, a GSA value of 1,850, and an OFA value of 69.4 and was configured of two ceramic filters having a size of 100 mm (W)×100 mm (D)×15 mm (H) and thus had a height of 30 mm. In this case, based on the photocatalytic ceramic filter structure volume of 0.3 L, the surface area of the photocatalytic film was 0.555 m$^2$.

Figure 14:
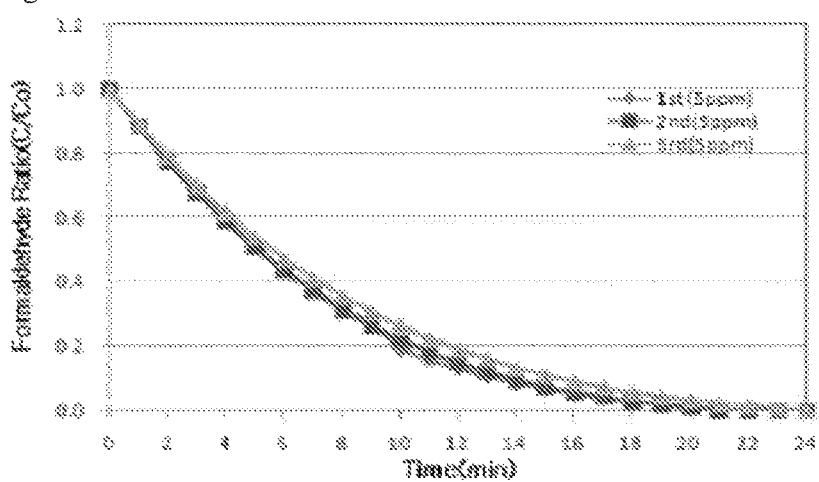
FIG. 14 is a graph showing the formaldehyde decomposition performance measured in Comparative Example 3.

The results obtained from three runs of the experiment are shown FIG. 14. The formaldehyde removal took an average of 22 minutes.

In addition, in order to compare formaldehyde decomposition performance under the same volume and similar surface area conditions as the photocatalyst-coated filter structure of Experimental Example 1, 10 ceramic filters were laminated so that a photocatalytic film surface area was 2.78 m$^2$ based on the photocatalytic ceramic filter structure volume of 1.5 L. According to the results obtained from three runs of the experiment, the formaldehyde removal took an average of 23 minutes.

From the above results, the following inferences can be made. Although a ceramic honeycomb filter is a structure that secures a large surface area, it can be seen that the area irradiated with light reaching the inner center of the ceramic filter is small due to the dense cell structure and light absorption at the surface. Therefore, it can be seen that a ceramic honeycomb structure is relatively limited as compared to a glass substrate and/or an aluminum honeycomb substrate in terms of a structure length that can produce an effective photocatalytic effect.

Therefore, it was found that a ceramic honeycomb photocatalytic air filter takes at least three times more time to decompose formaldehyde than a photocatalytic air filter formed of a glass material. The reason is as follows. A glass material has light-transmitting characteristics and thus allows light to be used to the maximum, whereas a ceramic material has light-absorbing characteristics unlike a glass material, so its efficiency is significantly lower than that of the glass material that enables maximum use of light. Also, unlike glass surfaces which do not have pores, an organic gas penetrates into pores of the ceramic material and thus takes more time to remove.

When the above results are summarized, it can be seen that the organic gas (formaldehyde) decomposition by a photocatalyst is effective when a structure does not significantly impede air flow and the photocatalyst has a large surface area, and the activity of the photocatalyst is further improved in a cell structure and/or a plate-shaped grid structure in which the UV transmittance or reflectance of the used substrate is high, and a photocatalytic air filter in which the structural material itself does not have porosity is most effective.

DESCRIPTION OF REFERENCE NUMERALS

1. Photocatalytic aluminum honeycomb structure
2. UVA-LED PCB
3. Photocatalytic-filter module housing

INDUSTRIAL APPLICABILITY

The glass and aluminum structure air filters including a photocatalytic precoat according to the present invention can be applied to various air purifiers and thus have high industrial applicability.

The invention claimed is:

1. A method of manufacturing a glass or aluminum structure air filter employing a photocatalytic precoat,
wherein a photocatalytic topcoat is applied to a glass or aluminum structure using a photocatalytic precoat solution as a binder, and
the precoat solution is prepared by mixing and reacting a photocatalytic topcoat solution, tetraethyl orthosilicate (TEOS), and methyl triethoxysilane (MTEOS), adding tetra-n-butyl titanate (TnBT), and then inducing a reaction.

2. The method of claim 1, wherein the precoat is formed on the glass or aluminum structure by forming a film by a coating process using one or more of a dip-coating process, a flow-coating process, and a spray-coating process, and drying in a drying oven at a temperature of 120° C. to 150° C. for 20 minutes to 30 minutes.

3. The method of claim 1, wherein the glass structure is an air filter structure formed of a glass material including one or more of a glass plate having a plate shape and a glass tube having a tube shape, and a photocatalytic film having a geometric surface area (GSA; units: $m^2/m^3$) value of 2,000 and an open frontal area (OFA; units: %) value of 69 is formed.

4. The method of claim 1, wherein the aluminum structure is configured to have a hexagonal or rectangular honeycomb shape, and has a GSA value of 1,490 and an OFA value of 96.

5. The method of claim 1, wherein sintering is performed at high temperature and thus bonding between the photocatalytic topcoat, the precoat, and the glass or aluminum structure is imparted, and the sintering is performed at a temperature range of 400° C. to 550° C. for a sintering time of 30 minutes to 2 hours.

6. The method of claim 1, wherein a glass plate and a glass tube are disposed in the air filter, and a GSA value is 1,310, and an OFA value is 44.

7. The method of claim 1, wherein a glass tube of the glass structure has a GSA value of 1,260 and an OFA value of 49.

8. The method of claim 1, wherein the glass structure is configured of a glass plate and a glass tube which are alternately disposed, and has a GSA value of 1,310 and an OFA value of 44.

* * * * *